United States Patent [19]
Hashimoto et al.

[11] Patent Number: 4,911,845
[45] Date of Patent: Mar. 27, 1990

[54] PROCESS AND APPARATUS FOR SEPARATION OF VOLATILE COMPONENTS

[75] Inventors: Koichi Hashimoto, Tokyo; Kohei Ninomiya, Ichihara, both of Japan

[73] Assignee: UBE Industries, Ltd., Japan

[21] Appl. No.: 51,364

[22] Filed: May 19, 1987

[30] Foreign Application Priority Data

May 20, 1986 [JP] Japan .................................. 61-113475

[51] Int. Cl.$^4$ ............................................ B01D 13/00
[52] U.S. Cl. .................................. 210/640; 210/416.1
[58] Field of Search .................... 210/640, 416.1, 254, 210/181; 202/172; 55/16, 158

[56] References Cited

U.S. PATENT DOCUMENTS

| | | | |
|---|---|---|---|
| 3,540,986 | 11/1970 | Guarino | 210/640 X |
| 4,067,805 | 1/1978 | Chiang et al. | 210/640 X |
| 4,316,774 | 2/1982 | Trusch | 210/640 X |
| 4,466,202 | 8/1984 | Merten | 34/32 X |

*Primary Examiner*—Frank Spear
*Attorney, Agent, or Firm*—Finnegan, Henderson, Farabow, Garrett & Dunner

[57] ABSTRACT

A process for the mutual separation of volatile components in a mixture comprising at least two volatile components, comprising the steps of: (1) heating a starting liquid comprising at least two volatile components to vaporize the starting liquid and form a vapor mixture comprising the volatile component, (2) compressing the vapor mixture to cause a rise in the temperature and pressure thereof, (3) applying the compressed vapor mixture to a membrane having a selective permeability to separate the vapor mixture into a membrane-permeated fraction and a non membrane-permeated fraction, (4) indirectly placing at least one of the fractions in contact with the starting liquid of step (1) via a heat transferring wall to use the heat of the contacted fraction to vaporize the starting liquid, and (5) recovering one or both of the membrane-permeated fraction and non membrane-permeated fraction; and an apparatus for a mutual separation of volatile components in a mixture comprising at least two volatile components, comprising: (1) an evaporator having at least one heat exchanger into which at least one fraction separated by a membrane separator of (3) is introduced, a starting liquid feeding side, an evaporation residue discharging side, and an optional auxiliary heater; to generate a vapor mixture, (2) a compressor to compress the vapor mixture, and (3) a membrane separator comprising a member having a selective permeability to separate the compressed vapor mixture into a membrane-permeated faction and a non membrane-permeated fraction.

10 Claims, 1 Drawing Sheet

PROCESS AND APPARATUS FOR SEPARATION OF VOLATILE COMPONENTS

BACKGROUND OF THE INVENTION

1. Field of the Invention

The present invention relates to a process and apparatus for the separation of volatile components in a gas phase using a membrane having a selective permeability. The present process and apparatus are energy-saving and industrially useful.

2. Description of the Related Art

Processes for the separation of individual components in a liquid comprising at least two volatile components, on the basis of their volatility, such as distillation, rectification and the like, are well-known and widely used in industry.

Processes for a liquid-phase separation of more than one component in a liquid using a membrane having a selective permeability are also well known and practically used. Recently, a process for gas-phase separation of gas components using a membrane having a selective permeability has been disclosed, but this process have not yet been developed fully for industrial application.

A process by which a liquid is heated by a heat exchanger to distill or concentrate the liquid is also well known and widely used. As is well known a thermodynamic phenomenon wherein the adiabatic compression of a gas causes a rise in the pressure and temperature thereof.

However, there is no known system for a mutual separation of more than one gas component, characterized by combining vaporization of a liquid using a heat exchanger, raising a pressure and temperature of a gas by adiabatic compression, and mutual separation of more than one gas component by a membrane having a selective permeability, resulting in a notable saving of energy costs by the use of an efficient heat recycling.

SUMMARY OF THE INVENTION

Therefore, the present invention provides a process for mutual separation of volatile components in a mixture comprising at least two volatile components, comprising the steps of:

(1) heating a starting liquid comprising at least two volatile components to vaporize the starting liquid and form a vapor mixture comprising the volatile components, (2) compressing the vapor mixture to raise the temperature and pressure thereof, (3) applying the compressed vapor mixture to a membrane having a selective permeability to separate the vapor mixture into a membrane-permeated fraction and a non membrane-permeated fraction, (4) indirectly placing at least one of said fractions in contact with the starting liquid of the step (1) via a heat transferring wall to utilize the heat of the contacted fraction to vaporize the starting liquid, and (5) recovering one or both of said membrane-permeated fraction and non membrane-permeated fraction.

The present inventions also provide an apparatus for a mutual separation of volatile components in a mixture comprising at least two volatile components, comprising:

(1) an evaporator having at least one heat exchanger into which at least one fraction separated by a membrane separator of (3) is introduced, a starting liquid feeding site, an evaporation residue discharging site and an optional auxiliary heater; to generate a vapor mixture;

(2) a compressor to compress said vapor mixture;

(3) a membrane separator comprising a membrane having a selective permeability to separate said compressed vapor mixture into a membrane-pemeated fraction and a non membrane-pemeated fraction.

DESCRIPTION OF THE PREFERRED EMBODIMENT

Figure 1:
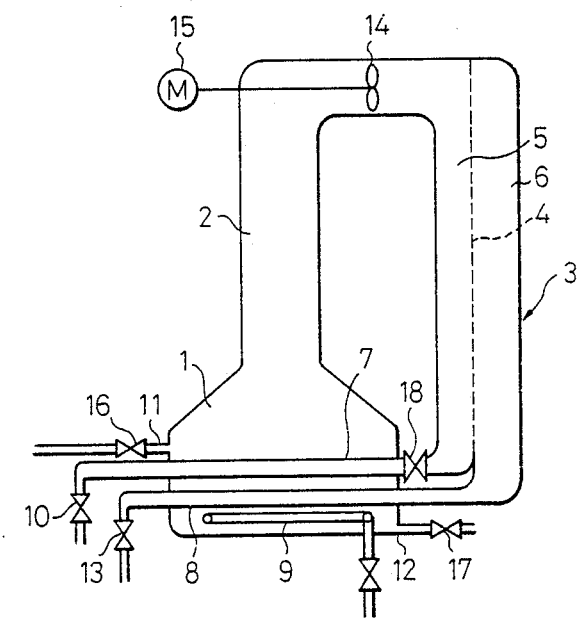
FIG. 1 is a schematical representation of an apparatus according to the present invention.

According to the present invention, since volatile components are mutually separated in a gas phase by a membrane having a selective permeability, it is not necessary for the components to be mutually separated to have different volatilities. Therefore, by appropriately selecting the membrane, various kinds of mixture can be separated. For example, mixtures comprising water and an organic substance which can be separated according to the present process include, water/methanol, water/ethanol, water/propanol, water/butanol, water/acetone, water/acetic acid, water/acetonitrile, water/acrylonitrile, water/benzene, water/ethyl acetate, water/phenol and the like. The present process also can be applied to the separation of a mixture comprising at least two organic substances, such as acetone/n-hexane, ethanol/acetone, styrene/ethylbenzene, benzene/aniline, and the like.

The evaporator used in the present invention is provided with at least one heat exchanger therein, a starting liquid feeding site and an evaporation residue discharging site, and an optional auxiliary heater. Since, according to the present invention, the mutual separation of a volatile composition does not utilize the difference in the volatilities of the different components, the evaporator does not need to have a fractional distillation function, and therefore, may be selected from conventional evaporators, such as natural circulation evaporator, forced circulation evaporator, thin-film evaporator, scraped surface evaporator, and the like.

According to the present invention, a vapor comprising volatile components generated in the abovementioned evaporator is introduced from the evaporator to a compressor, and compressed to cause a rise in the temperature and pressure thereof. The compressor can be selected from any conventional compressor used to compress a vapor at a high temperature, and such compressors include, for example, a Roots Blower type compressor, and an axial flow blower type compressor.

Next, the raised pressure of the vapor is used as a driving force for the separation of the vapor mixture, by a membrane having a selective permeation, into a membrane-permeated fraction and a non membrane-permeated fraction. Therefore, the membrane is selected according to kinds of components to be separated, their concentrations, and the like. For example, when separating a mixture comprising water and ethanol, if the concentration of ethanol is as low as less than 50% by weight in relation to the total weight of water and ethanol, a membrane, such as that made of silicone rubber, which preferentially permeates ethanol, is preferably used. On the other hand, if the concentration of ethanol is as high as more than 50% by weight in relation to the total weight of water and ethanol, a membrane such as a cellulose acetate membrane, a polyphenylene oxide membrane, a silica-alumina porous membrane or a polyimide membrane, which preferentially permeate water, is preferably used.

The membrane used in the present invention is preferably selected from those membranes which can be used at a temperature higher than 80° C. Polyimide membranes can be used at a temperature higher than 100° C., and therefore, are especially preferable. Among the most preferable polyimide membranes are aromatic polyimide membranes prepared from aromatic tetracarboxylic acid or its dianhydride reacted with aromatic diamine.

Polyimide membranes also are preferable for their permeability performance. The permeability of water $P'_{H_2O}$ is as high as 0.5 to $5 \times 10^{-5}$ cc/cm$^2$.sec.cmHg, preferably 0.1 to $5 \times 10^{31\ 3}$ cc/cm$^2$.sec.cmHg, although varying according to operating conditions.

The separation performance of polyimide membranes is also superior. Namely, in the separation performance of water and ethanol, the $P'_{H_2O}/P'_{EtOH}$ is as high as 50 to 400, preferably 100 to 300.

The membranes of the present invention are preferably of plane film type, tubular type or hollow fiber type. The bollow fiber type membranes are most preferable.

Among the vapor fractions separated by the membrane, the non membrane-permeated fraction is maintained at a high temperature and high pressure, and the membrane-permeated fraction is maintained at a high temperature but the pressure thereof is lowered. Therefore, either both of the fractions are separately, or one of the fractions is, introduced into a heated exchanger positioned in the above-mentioned evaporator to transfer the heat contained in the introduced vapor fraction(s) to the starting liquid, to reuse the heat for evaporation of the starting liquid. Accordingly, the heat exchanger may be a conventional vapor/liquid heat exchanger. For example, the heat exchanger can be constructed by positioning metal pipes in the evaporator.

Next, referring to the FIGURE, an embodiment and functional principle are explained in detail. In FIG. 1, a starting liquid comprising at least two volatile components is introduced from a starting liquid feeding site 11 into an evaporator 1. Next, a heat source such as steam is introduced into an auxiliary heater 9 to heat the starting liquid, resulting in evaporation of the starting liquid and generation of a vapor mixture comprising the volatile components. The vapor mixture then passes through a vapor conduit and entrainment separator 2 to separate entrainment.

The vapor is then compressed by a vapor compressor 14 driven by an electric motor 15, and vapor having an elevated temperature and pressure is introduced to a membrane separator 3.

The membrane separator 3 comprises a high pressure portion 5 and a low pressure portion 6 separated by a membrane 4 having a selective permeability. The high pressure portion 5 is maintained at a desired high pressure by manipulating a control valve 18, and the low pressure portion 6 is maintained usually at an atmospheric pressure by opening a valve 13 or at a desired subatmospheric pressure by connecting the valve 13 to a vacuum pump (not shown). The difference between the pressures of the high pressure portion 5 and the low pressure portion 6 provide the driving force needed to separate the vapor mixture into a membrane-permeated fraction and a non membrane-permeated fraction. The pressures of the high pressure portion 5 and low pressure portion 6, and therefore the difference of the pressures between these portions, are selected according to the kinds of components to be separated, concentrations thereof, the selection of a membrane, an the like.

Except for certain kinds of membranes such as silicone membrane, most membranes are preferantially permeable for water. In the case of water/ethanol, therefore, water is concentrated in a permeated fraction and the concentration of ethanol increases in a non-permeated fraction. Especially, the permeation rate of water through a polyimide membrane is high, and therefore, the polyimide membrane is preferably used for the separation of vapors of water and ethanol. In this case, the permeation rate of water is higher as the difference of pressure between the high pressure portion and low pressure portion becomes larger, and/or as the water concentration in the high pressure portion becomes higher.

The apparatus of the present invention is preferably totally heat-insulated in a heat insulator to carry out the vapor compression by the compressor 14 under a pseudo-adiabatic condition. As a result, a temperature of the compressed vapor is substantially higher than that of vapor in the evaporator 1. This elevated temperature is substantially maintained in both the non membrane-permeated fraction and membrane-permeated fraction. Therefore, one or both of the fractions is/are introduced into heat exchangers 7 and/or 8 to condense the volatile components, and the condensation heat is partially used to vaporize the starting liquid. Therefore, although when starting the operation it is necessary to supply heat via the auxiliary heater 9, once the operation starts this supply of heat via the auxiliary heater 9 can be stopped, or a small amount of heat may be supplied via the auxiliary heater 9, if necessary. This means that all or most of the heat necessary for the evaporation of the starting liquid is furnished through energy of vapor introduced via the compressor 14 and membrane separator 3.

The evaporation of the starting liquid in the evaporator 1 can be carried out batchwise or continually. In the batchwise operation, the starting liquid is introduced via the starting liquid feeding valve 16 at the starting liquid feeding side 11 into the evaporator 1, wherein the evaporation residue discharging valve 17 has been closed. After the starting liquid feeding valve 16 is closed, the evaporation starts, and after the evaporation is finished, both the valves 16 and 17 are opened to discharge an evaporation residue. Where the starting liquid substantially consists of volatile components, and therefore, all the starting liquid is vaporized, the discharge of the residue after each batch is not necessary. In the continual operation, the starting liquid is continually introduced via the starting liquid feeding valve 16 at the starting liquid feeding side 11 into the evaporator 1 at a rate suitable to supplement an amount of volatile components vaporized in the evaporator 1 and simultaneously, an evaporation residue is discharged via the evaporation residue discharging site 12 and the evaporation residue discharging valve 17. If the starting liquid substantially consists of volatile components, and therefore, all of the starting liquid is vaporized, continual discharge of the residue is not necessary. Moreover, a semi-continual operation can be carried out by intermittently introducing the starting liquid and/or intermittently discharging the evaporation residue.

Next, the heat-balance at a steady state during a continual operation according to the present invention is explained in detail. Heat introduced in the system of the present invention consists of heat carried by the starting liquid, heat introduced by the compressor 14, and heat introduced by the auxiliary heater 9; and heat discharged from the system consists of heat carried by condensed liquids (products) discharged from the heat exchangers, heat carried by the evaporation residue, and heat lost by radiation from surfaces of the apparatus. Now, if an amount of heat which is transferred via the heat exchangers 7 and/or 8 in the evaporator 1 to the starting liquid (that is, condensation heat and some sensible heat of the fractionated vapors) is less than an amount of heat necessary to vaporize the starting liquid, the shortage of heat must be supplemented by the auxiliary heater 9. Such a case may occur when, for example, the temperature of the starting liquid is too low. Note, the auxiliary heater is not necessarily positioned in the evaporator 1, but can be positioned outside the evaporator 1 to heat the starting liquid before it is introduced into the evaporator. This means that a desired steady state can be maintained by controlling the temperature of the starting liquid.

Next, a case may occur wherein an amount of heat supplied to the heat exchangers 7 and/or 8 in the evaporator 1 from the membrane separator 3 is much higher than an amount of heat necessary to vaporize the starting liquid in the evaporator 1. This may occur, for example, when an amount of heat carried by the starting liquid is too high; that is, the temperature of the starting liquid to be introduced is too high, and/or when an amount of heat introduced by the compressor 14 is too high. In such a case, the steady state can be recovered by lowering the temperature of the starting liquid to be introduced. As another method of recovering the steady state, the fractions (products) discharged from the heat exchangers 7 and/or 8 in the evaporator 1 can be removed before completely condensed, and then completely condensed by an external cooler (not shown).

Note, when the temperatures of the products and evaporation residue are rather high, heat carried by these materials can be recovered by additional heat exchangers (not shown).

According to the present invention, a starting liquid is vaporized by heating with heat exchangers to generate a vapor mixture, which is then compressed to elevate a pressure and temperature thereof. The elevated pressure of the vapor acts as a driving force for separation by a membrane of the vapor into a membrane-permeated fraction and a non membrane-permeated fraction, on the other hand, the difference in temperature between an elevated temperature of the compressed vapor, (i.e., the membrane-permeated fraction and/or the non membrane-permeated fraction) and an evaporation temperature of the starting liquid is used to recover heat contained in the vapor fractions via the heat exchanger to evaporate the starting liquid. Therefore, only a small amount of energy, i.e., energy introduced via a vapor compressor, heat necessary to heat the starting liquid to a temperature below the evaporation temperature of the starting liquid, and heat for heating an auxiliary heater, is necessary. Therefore the present separation system is very advantageous from the point of view of energy -saving.

EXAMPLES

The present invention will now be further illustrated by, but is no means limited to, the following examples.

EXAMPLE 1

Concentration of Ethanol

For purification of black crude sugar (containing molasses), aqueous ethanol having a concentration of about 80% is used, and impure ethanol having a concentration of about 60% is recovered. The recovered ethanol contains water, sugar, ash, pigments and other impurities originally contained in the crude sugar. Therefore, to reuse the recovered aqueous ethanol, it must be purified by eliminating the above-mentioned impurities and increasing the concentration of ethanol from about 60% to at least about 80%. For this purpose, aqueous ethanol was concentrated according to the present invention, as follows.

100 l of starting aqueous ethanol (ethanol 60 l + water 40 l) was changed into the apparatus schematically shown in FIG. 1, and steam was introduced into the auxiliary heater 9 to heat the starting aqueous ethanol to a temperature of 86° C. Evaporation started at this temperature. Then, the starting aqueous ethanol was continually introduced at a constant rate of 20 l/hour (ethanol 12 l/hour + water 8 l/hour), and an evaporation residue was continually discharged at a constant rate of 3 l/hour (ethanol 0.07 l/hour + water, sugar, ash and other purities). About 100 kcal/hour of heat was supplemented by steam via the auxiliary heater 9.

At 1 atm, the starting aqueous ethanol vaporized at a rate of 17 l/hour (ethanol 11.93 l/hour + water 5.07 l/hour). The heat for the evaporation was about 5610 kcal/hour. Vapor was compressed to 1.5 atm using a vapor compressor driven by a 1.1 kW axial power electric motor, with the result that the temperature of the vapor rose to 119° C. The energy was introduced by the compressor at about 950 kcal/hour. The compressed vapor flowed along and in contact with a silica-alumina porous membrane having a surface area of about 1 m$^2$, at a flow rate of 1.5 m/sec. During this procedure, the compressed vapor was separated into a non membrane-permeated vapor fraction and a membrane-permeated vapor fraction. Both fractions were introduced into different heat exchangers positioned in the evaporator, and a condensate from the non membrane-permeated fraction was obtained from an outlet of the heat exchanger at a rate of 13 l/hour (ethanol 11.91 l/hour, water 1.09 l/hour ethanol concentration about 84%), and another condensate from the membrane-permeated fraction was obtained at a rate of 4 l/hour (ethanol 0.02 l/hour, water 3.98 l/hour, ethanol concentration 0.5%).

By the above-mentioned heat exchange, about 3050 kcal/hour of heat was recovered from the non membrane-permeated fraction, and about 2440 kcal/hour of heat was recovered from the membrane-permeated fraction (total about 5490 kcal/hour). Therefore, about 90% of the heat used for evaporation of the starting aqueous ethanol was provided from heat recovered from the compressed vapor. This means that 20 l/hour of the starting aqueous ethanol was processed by about 1050 kcal/hour of newly introduced heat (about 100 kcal/hour of heat from the auxiliary heater plus about 950 kcal/hour of heat from the vapor compressor).

EXAMPLE 2

Concentration of Ethanol

In ethanol production, a fermentation broth containing about 10% of ethanol was obtained. Taking this into consideration, 10% aqueous ethanol as a model of the fermentation broth was concentrated according to the present process.

The same procedure as described in Example 1 was repeated, except that a temperature of the starting aqueous ethanol was about 100° C., and all of the starting aqueous ethanol was vaporized, and therefore, no evaporation residue was discharged. In this case, about 11,556 kcal/hour of heat was necessary for the evaporation, and heating by the auxiliary heater was not necessary. The vapor was compressed with a compressor driven by a 4 kW axial power electric motor to a pressure of 1.5 atm. In this case, about 3900 kcal/hour of heat was introduced into the system by the compressor, resulting in an elevation of the vapor temperature to about 139° C. A condensate from a membrane-permeated fraction was obtained at a rate of 13 l/hour (ethanol concentration at most 0.1%); and another condensate from a membrane-permeated fraction was obtained at a rate of 7 l/hour (ethanol concentration at least 30%).

378 kcal/hour of heat was recovered from the non membrane-permeated fraction via a heat exchanger in the evaporation, and 10,500 kcal/hour of heat was recovered from the membrane-permeated fraction via another heat exchanger in the evaporator (total 10,898 kcal/hour). Therefore, about 94% of the heat used for evaporation of the starting aqueous ethanol was provided by heat recovered from the vapor fractions. This means that 20 l/hour of the starting aqueous ethanol was processed by about 3900 kcal/hour of heat introduced by the vapor compressor.

EXAMPLE 3

Dehydration of Acrylonitrile

Although acrylonitrile can contain about 3% of water, the acrylonitrile used as a starting material for production of synthetic fibers was substantially anhydrous. Therefore, acrylonitrile saturated with water (about 3% water) was dehydryzed according to the present process.

The same procedure as described in Example 1 was repeated except that the starting aqueous acrylonitrile was introduced at a rate of 40 l/hour, and all of the starting aqueous acrylonitrile was vaporized. In this case, the boiling point was 24° C., and the heat for evaporation was 23,400 kcal/hour. The vapor was compressed with a vapor compressor driven by an electric motor to an atmospheric pressure. In this case, 2150 kcal/hour of heat was introduced by the compressor, resulting in an elevation of the vapor temperature to 100° C. The compressed vapor was then fractionated with a silica-alumina porous membrane. 1.2 l/hour of water in which acrylonitrile could not be detected was obtained from the membrane-permeated fraction. On the other hand, 38.8 l/hour of acrylonitrile in which water could not be detected was obtained from the non membrane-permeated fraction. About 720 kcal/hour of heat was recovered from the membrane-permeated fraction via a heat exchanger in the evaporator, and about 7436 kcal/hour of heat was recovered from the non membrane-permeated fraction via another heat exchanger in the evaporator (total 8156 kcal/hour). Therefore, about 35% of the heat used for evaporation of the starting acrylonitrile was provided by heat recovered from the vapor fractions. This means that 40 l/hour of the starting aqueous acrylonitrile was processed by 2150 kcal/hour of heat introduced by the vapor compressor.

EXAMPLE 4

Concentration of Ehtanol 400 l of starting aqueous ethanol (ethanol 40 l + water 360 l) was charged into a apparatus schematically shown in FIG. 1 and steam was introduced into the auxiliary heater 9 to heat the starting aqueous ethanol to a temperature of 99° C. evaporation started at this temperature. Then, the starting aqueous ethanol was continually introduced at a constant rate of 200 l/hour (ethanol 20 l/hour + water 180 l/hour), and no evaporation residue was discharged.

About 113,000 kcal/hour of heat was used for the evaporation. The vapor was compressed to 1.7 atm using a vapor compressor driven by a 22 kW electric motor resulting in an elevation of the temperature of the vapor to 146° C. Energy introduced by the compressor was about 19,000 kcal/hour. The compressed vapor flowed along and in contact with a polyimide hollow fiber membrane having a surface area of about 50 m² at a flow rate of about 1.0 m/sec. During this procedure, the compressed vapor was separated into a non membrane-permeated vapor fraction and a membrane-permeated vapor fraction. Both fractions were introduced into different heat exchangers positioned in the evaporator, and a concentrate from the non membrane-permeated fraction was obtained from an outlet of the heat exchanger at a rate of 35 l/hour (ethanol 21 l/hour, water 14 l/hour, ethanol concentration about 60%), and another concentrate from the membrane-permeated fraction was obtained at a rate of 165 l/hour (ethanol negligible, water 165 l/hour, ethanol concentration 0.1% under).

By the above-mentioned heat exchange, about 12,000 kcal/hour of heat was recovered from the non membrane-permeated fraction, and about 94,000 kcal/hour of heat was recovered from the membrane-permeated fraction (total about 106,000 kcal/hour). Therefore, about 94% of heat used for the evaporation of the starting aqueous ethanol was provided from heat recovered from the compressed vapor. This means that 200 l/hour of the starting aqueous ethanol was processed by about 18,900 kcal/hour of newly introduced heat (about 18,900 kcal/hour of heat from the vapor compressor).

The above-mentioned polyimide hollow film membrane is formed from anaromatic polyimide obtained from aromatic tetracarboxylic acid or its dianhydride reacted with aromatic diamine, and has a water permeability $P'_{H_2O}$ of more than $3 \times 10^{-3}$ cc/cm².sec.cm Hg, and a separation performance $P'_{H_2O}/P'_{EtOH}$ of more than 200.

We claim:

1. A process for mutual separation of volatile components in a mixture comprising at least two volatile components, comprising the steps of:
   (1) heating a starting liquid comprising at least two volatile components to vaporize the starting liquid and form a vapor mixture comprising the volatile components, (2) compressing the vapor mixture to cause a rise in a temperature and pressure thereof, (3) applying the compressed vapor mixture to a membrane having a selective permeability to separate the vapor mixture into a membrane-permeated fraction and a non membrane-permeated fraction, (4) indirectly placing at least one of said fractions in contact with the starting liquid of step (1) via a heat transferring wall to utilize the heat of the contacted fraction as heat to vaporize the starting liquid, and (5) recovering one or both of said membrane-permeated fraction and non membrane-permeated fraction.

2. A process according to claim 1 wherein in step (2), a pressure of the vapor mixture is increased to a pressure higher than an original pressure by 0.1 atm to 10 atm.

3. A process according to claim 1 wherein in step (2), a temperature of the vapor mixture is increased to a temperature higher than an original temperature by 10° C. to 300° C.

4. A process according to claim 1 wherein the mixture is selected from the group consisting of mixtures of water/methanol, water/ethanol, water/propanol, water/buthanol, water/acetone, water/acetic acid, water/acetonitrile, water/acrylonitrile, water/benzene, water/ethyl acetate, and water/phenol.

5. A process according to claim 1 wherein the mixture is selected from the group consisting of acetone/n-hexane, ethanol/acetone, styrene/ethylbenzene, and benzene/aniline.

6. A process according to claim 1 wherein the membrane having a selective permeability is selected from the group consisting of silicone rubber membrane, cellulose acetate membrane, polyphenylene oxide membrane, and silica-alumina porous membrane.

7. A process according to claim 1 wherein the membrane having a selective permeability is formed from an aromatic polyimide obtained from aromatic tetracarboxylic acid or its dianhydride reacted with aromatic diamine.

8. An apparatus for mutual separation of volatile components in a mixture comprising at least two volatile components, comprising:

(1) an evaporator having at least one heat exchanger into which at least one fraction separated by a membrane separator of (3) is introduced, a starting liquid feeding side, an evaporation residue discharging side and an optional auxiliary heater; to generate a vapor mixture;

(2) a compressor to compress said vapor mixture;

(3) a membrane separator comprising a membrane having a selective permeability to separate said compressed vapor mixture into a membran-permeated fraction and a non membran-permeated fraction.

9. An apparatus according to claim 8 wherein the membrane having a selective permeability is selected from the group consisting of silicone rubber membrane, cellulose acetate membrane, polyphenylene oxide membrane, and silica-alumina porous membrane.

10. An apparatus according to claim 8 wherein the membrane having a selective permeability is formed from an aromatic polyimide obtained from aromatic tetracarboxylic acid or its dianhydride reacted with aromatic diamine.

* * * * *